(12) United States Patent
Skaggs

(10) Patent No.: US 6,626,829 B1
(45) Date of Patent: Sep. 30, 2003

(54) LARYNGOSCOPE AND METHOD

(75) Inventor: Eddie W. Skaggs, 3400 Ottomeyer Rd., High Ridge, MO (US) 63049

(73) Assignees: Eddie W. Skaggs, High Ridge, MO (US); George R. Schoedinger, III, St. Louis, MO (US); John B. Weltmer, St. Louis, MO (US)

( * ) Notice: Subject to any disclaimer, the term of this patent is extended or adjusted under 35 U.S.C. 154(b) by 0 days.

(21) Appl. No.: 09/683,939

(22) Filed: Mar. 5, 2002

(51) Int. Cl.⁷ ............................................. A61B 1/267
(52) U.S. Cl. ..................................... 600/190; 600/195
(58) Field of Search ............................. 600/185–196, 600/240, 210

(56) References Cited

U.S. PATENT DOCUMENTS

| | | |
|---|---|---|
| 3,426,749 A | 2/1969 | Jephcott |
| 3,826,248 A | 7/1974 | Gobels |
| 4,579,108 A | 4/1986 | Bauman |
| 4,583,527 A | 4/1986 | Musicant et al. |
| 4,834,077 A | 5/1989 | Sun |
| 4,878,486 A | 11/1989 | Slater |
| 5,065,738 A | 11/1991 | Van Dam |
| 5,347,995 A * | 9/1994 | Slater et al. ............... 600/190 |
| 5,438,976 A | 8/1995 | Nash |
| 5,571,071 A | 11/1996 | Shapiro |
| 5,638,812 A | 6/1997 | Turner |
| 5,676,635 A | 10/1997 | Levin |
| 5,743,849 A | 4/1998 | Rice et al. |
| 5,762,638 A | 6/1998 | Shikani et al. |
| 5,984,863 A * | 11/1999 | Ansari ......................... 600/185 |
| 6,231,505 B1 * | 5/2001 | Martin ......................... 600/190 |

FOREIGN PATENT DOCUMENTS

| | | | |
|---|---|---|---|
| DE | 19534652 A | * | 3/1997 |
| EP | WO 98/58990 | * | 12/1998 |

OTHER PUBLICATIONS

US 2003/0018239 A1; Jan. 23, 2003; Cartledge et al.*
PriMedco Anesthesia and Respiratory Accessories; Aug., 2001; pgs., cover page, 87–126; PriMedCo, Largo, Florida, USA.
Armstrong Medical Equipment; 2001; pgs., cover page, 102–103; Armstrong Medical Industries, Inc., Lincolnshire, IL, USA.
Mercury Medical Intubation Products; 2001; pgs., cover page, 1–19; Mercury Medical, Clearwater, FL, USA.

* cited by examiner

Primary Examiner—Gregory Huson
Assistant Examiner—Khoa Huynh
(74) Attorney, Agent, or Firm—Blackwell Sanders Peper Martin LLP

(57) ABSTRACT

A coated laryngoscope blade is provided wherein the coating is permanently affixed to a blade body and provides a resilient cushion to reduce the possibility of damage to a patient's teeth and/or soft tissue in the mouth and throat area. The coating may be applied by a method not requiring an expensive mold or tooling and is adapted for application to any size or shape of currently existing laryngoscope blade without the necessity of making tooling.

10 Claims, 2 Drawing Sheets

LARYNGOSCOPE AND METHOD

BACKGROUND OF INVENTION

The present invention relates to a laryngoscope blade for use in combination with a laryngoscope handle.

A laryngoscope is a medical device typically used during a surgical procedure. It is typically used by an anesthetist to assist in the intubation of a patient. Intubation is the insertion of a tube into the larynx for the passage of a gas such as an anesthetizing gas. The laryngoscope blade assists in displacing the epiglottis to provide access to the larynx while passing the tube. The laryngoscope blade also helps keep the tongue out of the way and can be used to apply pressure to the lower jaw for moving the lower jaw during the insertion of the tube.

Laryngoscopes may also be used for the examination of a patient's larynx without intubation.

Laryngoscopes are typically fitted with a light which can be in the form of a light bulb carried by the blade or a fiber optic cable, which allows the source of light to be remote from the point that light is emitted from the blade. Typically the lights are powered by a battery carried in the handle of the laryngoscope.

There are many types of laryngoscope blades used today and generally they will have a channel along the blade to help guide the endotracheal tube during insertion into the larynx. Such blades have complex contours and shapes, which vary immensely by brand and type.

It is important that the laryngoscope blade be rigid, durable and sterilizable. To achieve these goals, the laryngoscope blades have been made of metal, for example, stainless steel or chrome plated brass. While this achieves the goals of rigidity, sterilizability and durability, the use of metal has created problems, particularly with damage to teeth. There is considerable pressure applied to displace the soft tissue and tongue during laryngoscopy and this can result in dentition damage. Individual airway anatomy varies, resulting in a higher degree of difficulty in placing the endotracheal tube in a certain population of patients. Increased difficulty results in an increased incidence of dentition damage.

Many solutions have been offered for reduction of tooth damage, for example, the application of a non-permanent coating to the blade. One example of this is the application of beeswax to the blade in a selected area. There is also known the temporary adhesive attachment of polymeric sheets to the blade also in selected areas. There is also known sheaths that may be removably placed over the blade. The foregoing devices are meant for one time use after which the protective covering is disposed of and replaced.

The use of such temporary covers poses problems because during laryngoscopy frequent adjustments are made in the position of the blade while in contact with the patient's dentition and soft tissue. Such positional changes can move temporary covering devices relative to the underlying blade or even cause their separation. Also, they may become displaced and provide ineffective cushioning. In the example of beeswax, beeswax has for all practical purposes, no resilience and can be easily sheared and deformed permanently by patient's teeth providing little if any protection for the teeth during use of the laryngoscope. Also, there is a risk that a piece of the beeswax may become separated from the blade which could result in aspiration of the patient. Also, an increase in time for preparation of the blade with beeswax is required. In the case of an adhesively applied sheet, time must be devoted by operating room personnel to prepare the laryngoscope for use and then time must be spent removing the adhesively applied layer of sheet material. Such a sheet may also require trimming to fit. Again, temporarily applied material may be dislodged during laryngoscopy resulting in no dentition protection. Further, because there are many sizes and shapes of blades used, a large inventory of sheets is required. In the case of a sheath which has the blade inserted thereunto similar problems exist. The sheath may become loosened during use and can hamper visualization of the larynx. It may also obscure light from the source of light, if not applied correctly to the blade and would also require a large inventory of different sizes and shapes because of the different sizes and shapes of blades used in an operating room. Although the sheath will cover substantially all of the exposed metal of the blade, the adhesively backed layers can leave a substantial portion of the metal of the blade exposed for possible contact with the patient's teeth. The sheath also, because of its need to be more universal, may impair the functionality of the blade particularly when the blade has complex contours and channels to facilitate the insertion of an endotracheal tube or other functions for which the laryngoscope is used.

There is thus a need for an improved laryngoscope and more particularly an improved laryngoscope blade.

SUMMARY OF INVENTION

The present invention involves the provision of a laryngoscope having a handle and a blade. The blade has permanently affixed thereto a resilient or elastic coating that is resistant to shearing or cutting by a patient's teeth, and conforms substantially to the entire contour of the blade portion on which it is permanently affixed. The resilient coating encases a substantial portion of the blade along the length thereof providing a covering for top and bottom surfaces thereof and conformance to the complex contour of the blade, therefore, providing a fully cushioned and non-displaceable surface. Should the permanently affixed coating become damaged or excessively worn, the coating may be removed and replaced. The coating is meant for non-disposable use and is well adapted for use with numerous patients. The coating is easily cleaned and sterilized and maintains its integrity for many uses.

The present invention also allows for the provision of a method of making an improved laryngoscope blade with a permanently affixed resilient coating.

DETAILED DESCRIPTION

Figure 1:
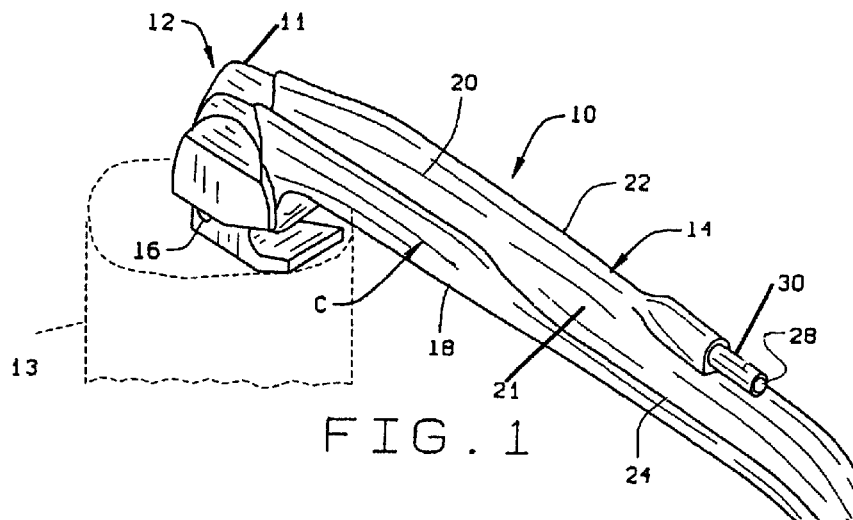
FIG. 1 is a perspective view of a coated laryngoscope blade constructed in accordance with the teachings of the present invention.
Figure 2:
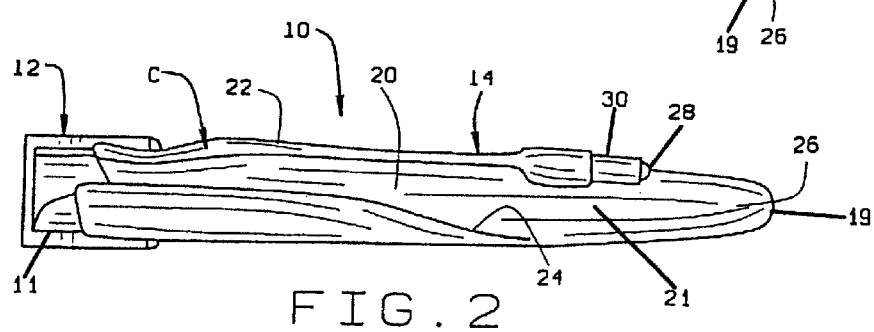
FIG. 2 is a top plan view of the coated laryngoscope blade of FIG. 1.
Figure 3:
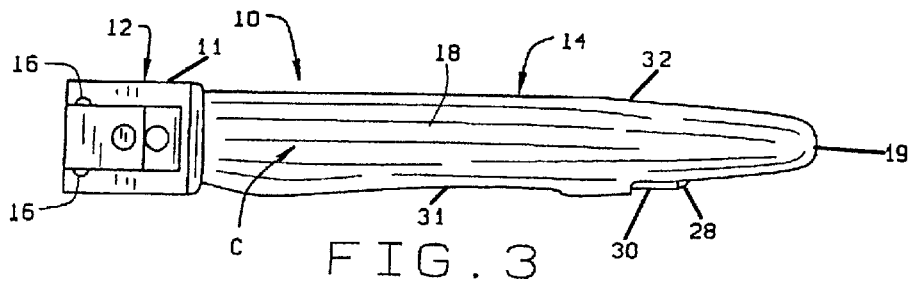
FIG. 3 is a bottom plan view of the coated laryngoscope blade of FIG. 1.
Figure 4:
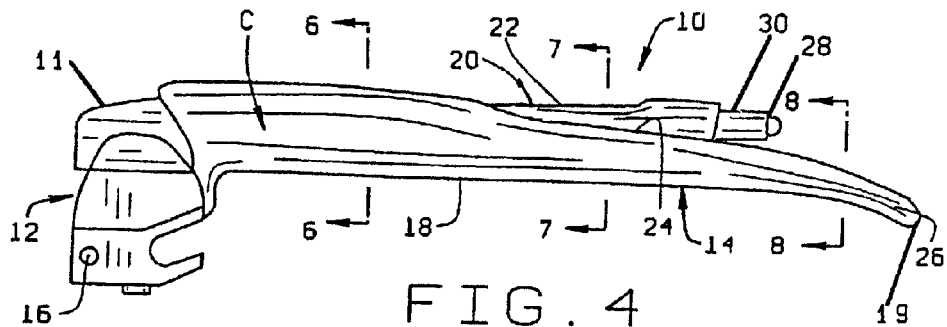
FIG. 4 is a right side elevation view of the coated laryngoscope blade of FIG. 1.
Figure 5:
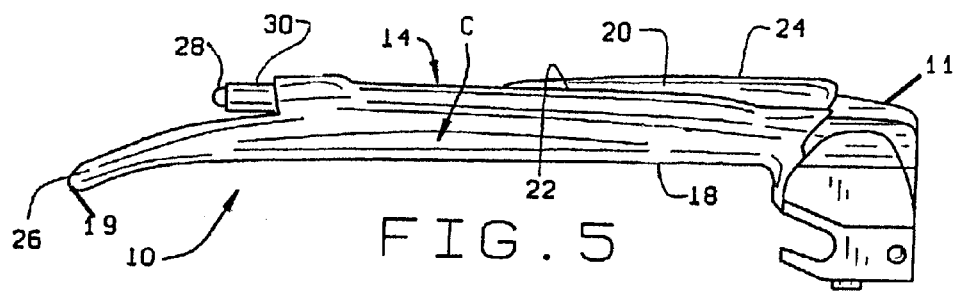
FIG. 5 is a left side elevation view of the coated laryngoscope blade of FIG. 1.

The laryngoscope blade 10 has a body 11 constructed in the usual manner and it may be supplied by any of the known manufacturers of such blade bodies. The blade 10 has an end section 12 (part of the body 11) for attachment to a handle 13 (shown partially and in phantom) and a blade section 14. Any suitable attachment means for releasably mounting the blade 10 to the handle 13 may be provided as is also known in the art. As shown, the end section 12 of the body 11 is typically provided with opposed spring biased balls or detents 16 for releasably locking engagement with complimentary shaped recesses (not shown) in the handle as is well known in the art. An electrical connection (not shown) can also be used to provide electrical current from batteries (not shown) carried in the handle 13 for powering a light 28 as is known in the art.

Figure 6:
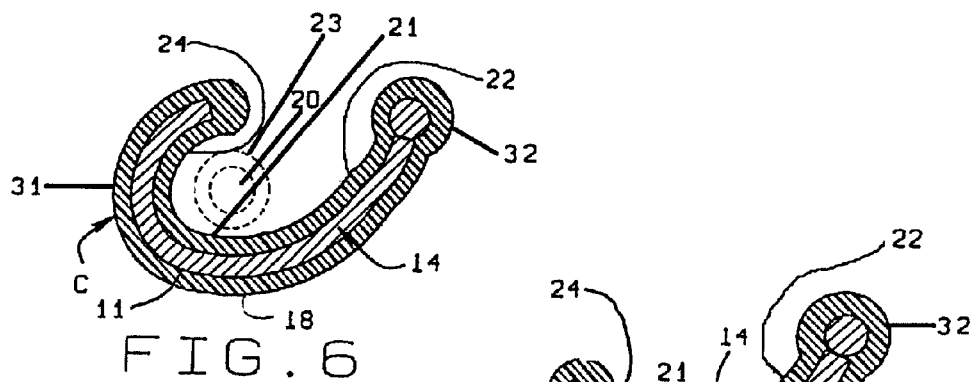
FIG. 6 is an enlarged sectional view of the coated laryngoscope blade as shown along lines 6—6 of FIG. 4.
Figure 7:
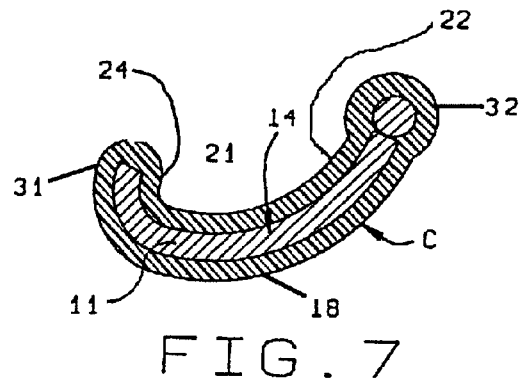
FIG. 7 is an enlarged sectional view of the coated laryngoscope blade as shown along lines 7—7 of FIG. 4.
Figure 8:
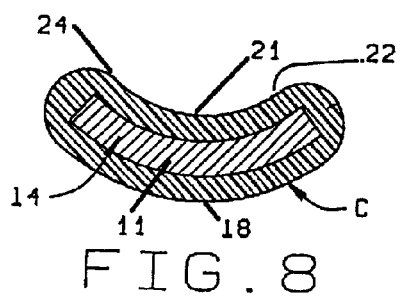
FIG. 8 is an enlarged sectional view of the coated laryngoscope blade as shown along lines 8—8 of FIG. 4.

The blade 10 generally has a smooth bottom surface 18 running from its free end 19 toward the attached end 12. An upper surface 21 is also provided and has an open side channel 20 provided therein. In cross section as best seen in FIG. 6 the channel can be generally C-shaped or any other suitable shape as is known in the art. The channel 20 is used to facilitate the insertion of a breather tube 23, a portion of which is shown in phantom in FIG. 6. The open channel 20 is generally defined by opposed smooth and sloping surfaces 22, 24 which terminate in section 26 opposite the handle in the end section 12.

In the illustrated embodiment, a light bulb 28 is received in a bulb receptacle 30 along the smooth and sloping surface 22. The bulb 28 is directed to project light toward the free end 19 of the blade 10 and downwardly into the patient's larynx and/or oral cavity during use and insertion of the blade 10. As is known in the art, a fiber optic cable can be used having its light projecting end positioned where the bulb 28 is positioned. The bulb 28 may then be positioned elsewhere, e.g., in the handle or adjacent the end section 12. The bulb 28 or the light transmitting end of the fiber optic cable will be on the exterior of the coating as hereinafter described.

The size and shape of the blade 10 including the top and bottom surfaces 18,21 channel 20 end sections 12 and 26 etc. may vary as desired. The present invention can be easily adapted to any size, shape or contour of blade. The size and shape used will be determined by the patient's mouth and throat and/or user's preference.

Typically, laryngoscope blade bodies are made from stainless steel or chrome plated brass. They have relatively smooth undersurfaces and are characterized by an absence of sharp or pointed edges or portions. They are easily sterilized. The blade body 11 has a coating C that substantially encases the blade body from its end 11 toward the end section 12 allowing for an opening therein for the light 28 and if desired, receptacle 30 for the transmission of light and access to the light 28 for maintenance. Alternately, at least the tooth engaging surfaces of the blade are coated with the coating C as described below and preferably the parts of the blade body 11 normally making contact with the oral pharyngeal mucosa.

The coating C is smooth, resilient and elastic, is shear and cut resistant under the normal forces, such as a biting force or force applied by the user, anticipated from a patient or applied by the user and is permanently affixed to the blade. The coating overlies a substantial portion of the top and bottom surfaces of the blade and extends along a substantial portion of the length of the blade. By permanently affixed, it is meant that the coating is either adhered to and/or mechanically locked in place on the blade or otherwise resistant to easy separation from the blade body 11. It is not meant to mean that the coating cannot be removed by solvents, cutting or other suitable removal methods for repair or replacement. The blade 10 has upper and lower surfaces 21, 18 and side edges 31, 32. The surfaces may have complex contours, which typically make many methods of application of the coating, for example, by molding impractical, particularly in view of the large number of sizes and shapes of blades currently in use. The present invention provides a coating and a method of coating the blade body adaptable for essentially any size or shape of blade without the need for expensive tooling or molding methods. Preferably, the coating C is latex free since some patients have an adverse reaction to latex. A plastisol (a liquid mixture of polymer and plasticizer) coating such as polyvinyl chloride or vinyl may be used. The coating is preferred to be at least about thirty mils (0.030 inches) and preferably in the range of between about thirty mils and about one hundred eighty seven mils (0.187 inches) and most preferably in the range of between about sixty mils (0.060 inches) and about one hundred twenty mils (0.120 inches). The more contours the coating can encase, the better permanent affixing of the coating to the blade body 11 through mechanical locking. The coating is resilient and elastic and under normal forces applied by a patient will not substantially permanently deform. Although some permanent deformation may occur, it will be minor and the coating will, from each application of force, regain at least about 80% of its original shape and thickness over the tooth engaging area. Some scarring, scratching and deformation may occur from each application of biting force, but it is minor and the coating will cushion the teeth to reduce tooth damage. The coating C is also cut and is shear resistant to retain the coating intact on the blade.

The coating C is preferably applied to the body 11 in liquid form and may be applied by well-known dip coating or dip molding techniques. The coating C may also be spray applied. The coating is preferably applied as a viscous liquid, and then allowed to cure to its resilient and elastic condition. In the construction of the coated blade, the light source may be either present or absent during the coating process and then a portion of the coating C removed to expose the light bulb or transmitting end of the fiber optic cable or the bulb may be absent during coating and a portion of the coating removed to expose the bulb receptacle 30 to allow for the insertion of the bulb 28. The coating C allows for yielding of the coating for cushioning of the teeth and/or other soft tissue in the mouth and/or throat of the patient. By applying the coating in liquid form, the coating C can conform to the complex contours of a blade without the necessity of using expensive molding devices and/or tooling. Also, the reflectivity or surface finish of the coating may be adjusted by adjusting the formulation of the liquid coating material eliminating the need for subsequent work on the coating to obtain the desired surface finish. By having a smooth finish such as a mat or pebbled finish, reflective glare can be reduced as compared to a gloss finish. The color of the coating may also be selected to achieve various end goals, for example, the control of reflection. A particularly preferred color is a silver gray with a matte or non-gloss finish. However, other colors may be utilized as desired, providing an additional advantage over blades that have exposed metal.

Cleaning of the laryngoscope blade 10 prior to or after use can be easily accomplished by known sterilization techniques. A preferred sterilization technique is a cold technique using gluteraldehyde as a sterilizing agent. Also, heat sterilization may be used so long as the temperature does not exceed that which will damage the coating. Other sterilization techniques as are known may also be employed so long as they do not adversely degrade the coating. Since the coated laryngoscope blade 10 will elastically deform under the applied tooth force, the teeth and/or soft tissue of a patient will be protected during use. It is anticipated that the coating C will wear some during use but not appreciably during a single use. Because of the potential for wear, the blade should be inspected for integrity prior to use. When excessive wear of the coating has resulted, the blade need not be disposed of. The coating may be removed by known removal techniques such as cutting the coating and peeling it from the blade, heating or solvent removal. The blade body 11 may be then subsequently re-coated for continued use by returning to the manufacturer for re-coating. From the foregoing, it will be appreciated that the coated laryngoscope blade offers an increased margin of comfort and safety to the patient reducing the potential for damage to teeth and/or soft tissue in the mouth and/or throat area of a patient during laryngoscopy because the coated blade substantially conforms to the original shape of a laryngoscope blade, the skill of the laryngoscopist is not compromised by use of the coated blade and no additional or special preparation is required before each use. Also, because the coating is permanent it does not require extra time for application and removal as do the temporary devices. The laryngoscopist need not concern himself with learning to use a new type or shape of blade. The blade 10 with coating and its use are thus substantially the same as the uncoated blade body while providing though an increased margin of safety without substantial cost in time or money.

Thus, there has been shown and described a novel laryngoscope and laryngpscope blade for use by medical personnel which fulfills the objects and advantages sought therefor. Many changes, modifications, variations and other uses and applications of the present unit will, however, become apparent to those skilled in the art after considering this specification and the accompanying drawings. All such changes, modifications, variations, and other uses and applications which do not depart from the spirit and scope of the present invention are deemed to be covered by the invention which is limited only by the claims which follow.

What is claimed is:

1. A laryngoscope blade comprising:
   an elongate blade body having top and bottom surfaces and side edges and means operable to connect the blade body to a handle; and
   a resilient polymeric coating secured to the blade body overlying a substantial portion of each of the top and bottom surfaces along a substantial portion of the length of the blade body, said coating being permanently affixed to the blade body, resistant to biting through and substantially elastically deformable.

2. The laryngoscope blade as set forth in claim 1 wherein the coating encases a substantial portion of the blade body.

3. The laryngoscope blade as set forth in claim 1 wherein the coating includes polyvinyl chloride.

4. The laryngoscope blade as set forth in claim 1 wherein the coating includes vinyl.

5. The laryngoscope blade as set forth in claim 1 wherein the coating is substantially latex free.

6. A method of forming a cushioned laryngoscope blade comprising:
   forming a laryngoscope blade body of metal, said blade body having top and bottom surfaces, side edges, a free end and an end structured for attachment to a handle;
   applying, as a liquid, a coating of polymeric material to encase a substantial portion of the blade body from the free end toward the attachment end; and
   curing the coating whereby the cured coating is resilient, resistant to biting through, substantially elastically deformable and is permanently affixed to the blade body.

7. The method as set forth in claim 6, including forming an opening in the coating to expose a light source.

8. The method as set forth in claim 6, wherein the liquid coating is applied by dipping.

9. The method as set forth in claim 6 wherein the liquid coating is applied by spraying.

10. A method as set forth in claim 6 including:
    evaluating the cured coating for wear;
    removing the worn cured coating and thereafter applying as, a liquid, a new coating of polymeric material to encase a substantial portion of the blade body from the free end toward the attachment end; and
    curing The new coating whereby the new cured coating is resilient, resistant to biting through, substantially elastically deformable and is permanently affixed to the blade body.

* * * * *

UNITED STATES PATENT AND TRADEMARK OFFICE
CERTIFICATE OF CORRECTION

PATENT NO. : 6,626,829 B1  Page 1 of 1
DATED : September 30, 2003
INVENTOR(S) : Eddie W. Skaggs It is certified that error appears in the above-identified patent and that said Letters Patent is hereby corrected as shown below:

Column 5,
Line 41, delete "laryngpscope" and replace with -- laryngoscope --;

Column 6,
Line 46, after the word "curing", delete "The" and replace with -- the --.

Signed and Sealed this

Eleventh Day of November, 2003

JAMES E. ROGAN
*Director of the United States Patent and Trademark Office*